United States Patent [19]
Ouchi

[11] Patent Number: 6,086,565
[45] Date of Patent: Jul. 11, 2000

[54] SYRINGE FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/157,139

[22] Filed: Sep. 18, 1998

[30] Foreign Application Priority Data

Oct. 9, 1997 [JP] Japan ..................................... 9-276982

[51] Int. Cl.⁷ ............................ A61M 5/00; A61M 11/00
[52] U.S. Cl. ......................... 604/187; 604/93; 604/264; 606/211
[58] Field of Search .................. 604/187, 20–22, 604/2, 93, 95, 264, 48; 606/49, 41, 45–50, 205, 211; 607/104, 105, 115, 116, 120, 122, 2

[56] References Cited

U.S. PATENT DOCUMENTS 5,336,222  8/1994  Durgin, Jr. et al. .................... 606/50
5,855,590  1/1999  Malecki et al. ......................... 606/205

FOREIGN PATENT DOCUMENTS 57-126201  8/1982  Japan .

*Primary Examiner*—Ronald Stright
*Assistant Examiner*—Michael J. Hayes
*Attorney, Agent, or Firm*—Greenblum & Bernstein P.L.C.

[57] ABSTRACT

A syringe for an endoscope including a flexible sheath having an operating part connected to a proximal end portion thereof. A flexible fluid transfer tube is axially movably inserted in the sheath. A hollow needle communicably provided at the distal end of the fluid transfer tube is projected from and withdrawn into the distal end of the sheath by axially moving the fluid transfer tube with the operating part. A mucous membrane holding member adapted to be pressed against a mucous membrane surface is attached to the distal end of the sheath through a connecting member in such a manner as to face the distal end of the sheath across a predetermined space from a position ahead of the distal end of the sheath.

6 Claims, 4 Drawing Sheets

SYRINGE FOR ENDOSCOPE

BACKGROUND OF THE INVENTION

The present disclosure relates to subject matter contained in Japanese Patent Application No. 9-276982 (filed on Oct. 9, 1997), which is expressly incorporated herein by reference in its entirety.

1. Field of the Invention

The present invention relates to a syringe used to inject a liquid medicine or the like into a body cavity through an endoscope.

2. Description of the Prior Art

In general, a syringe for an endoscope is arranged as follows. A flexible fluid transfer tube with a hollow needle at the distal end thereof is axially movably inserted in a sheath. The needle is projected from and withdrawn into the distal end of the sheath by actuating the fluid transfer tube to move axially at the proximal end of the sheath.

To give an injection into a body cavity with such a syringe endoscopically, the needle projecting from the distal end of the sheath is stuck into the affected part. At this time, it may be difficult to accurately stick the needle into the target affected part because the internal organs are active and moving at all times. In particular, in the case of the esophagus, in which the mucous membrane surface is always vibrated by the beating of the heart, it is very difficult to stick the needle into the correct position.

SUMMARY OF THE INVENTION

An object of the present invention is to provide a syringe for an endoscope that is designed so that the needle can be accurately and safely stuck into even a mucous membrane surface moving vigorously.

Other objects and advantages of the present invention will become apparent from the following detailed description of an illustrated embodiment of the invention.

According to the present invention, there is provided a syringe for an endoscope that includes a flexible sheath having an operating part connected to a proximal end portion thereof. A flexible fluid transfer tube is axially movably inserted in the sheath. A hollow needle is provided at the distal end of the fluid transfer tube in communication with it. The needle is projected from and withdrawn into the distal end of the sheath by axially moving the fluid transfer tube with the operating part. The syringe further includes a mucous membrane holding member adapted to be pressed against a mucous membrane surface. The mucous membrane holding member is attached to the distal end of the sheath through a connecting member such that the mucous membrane holding member faces the distal end of the sheath across a predetermined space from a position ahead of the distal end of the sheath.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

An embodiment of the present invention will be described below with reference to the accompanying drawings.

Figure 1:
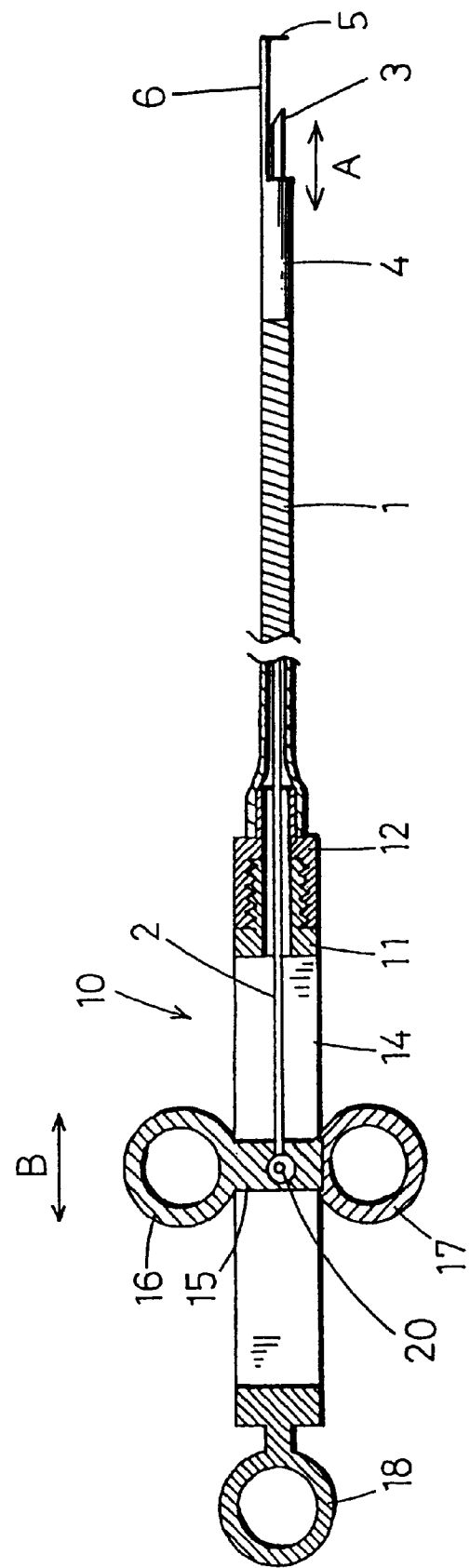
FIG. 1 is a side view of the whole arrangement of a syringe for an endoscope according to an embodiment of the present invention, in which an operating part of the syringe is shown in a sectional view.

FIG. 1 shows the whole arrangement of a syringe for an endoscope. A flexible sheath 1 is removably inserted into an instrument-inserting channel of an endoscope (not shown). As the sheath 1, a coil pipe is used which is formed by close-winding a thin stainless steel wire, for example, with a uniform diameter.

A fluid transfer tube 2 is axially movably inserted in the sheath 1 over the entire length thereof. The fluid transfer tube 2 is formed from a flexible tube. A hollow needle 3 is communicably joined to the distal end of the fluid transfer tube 2 to extend straightforward. The needle 3 is adapted to be stuck into the mucous membrane in a body cavity. In this embodiment, the needle 3 is formed by diagonally cutting a distal end portion of the fluid transfer tube 2. However, the needle 3 may be a needle of a metallic or plastic material that is secured to the distal end of the fluid transfer tube 2.

Figure 2:
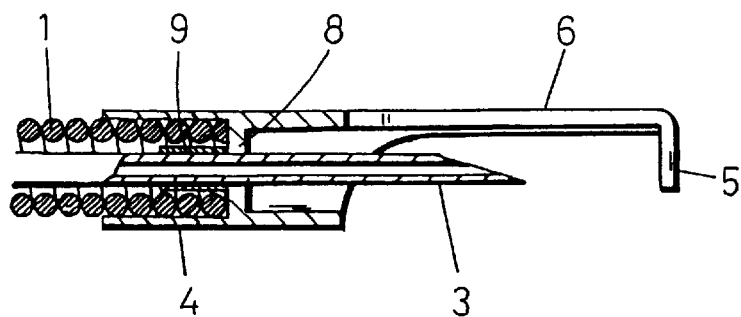
FIG. 2 is a sectional side view of a distal end portion of the syringe according to the embodiment of the present invention, showing a state where a needle of the syringe projects from the distal end of a sheath.

As shown in the enlarged view of FIG. 2, a mucous membrane holding member 5 is provided to face the distal end of the sheath 1 across a predetermined space to hold mucous membrane when stuck with the needle 3. The mucous membrane holding member 5 is integral with a connecting member 6 that connects with the distal end of the sheath 1. The mucous membrane holding member 5 is formed by bending the distal end portion of the connecting member 6 through approximately right angles in a hook shape.

The connecting member 6 is integral with a tubular member 4 fitted and secured to the distal end of the sheath 1. The connecting member 6 extends forward from the tubular member 4. With this arrangement, the mucous membrane holding member 5 is fixedly disposed in a predetermined position.

Figure 3:
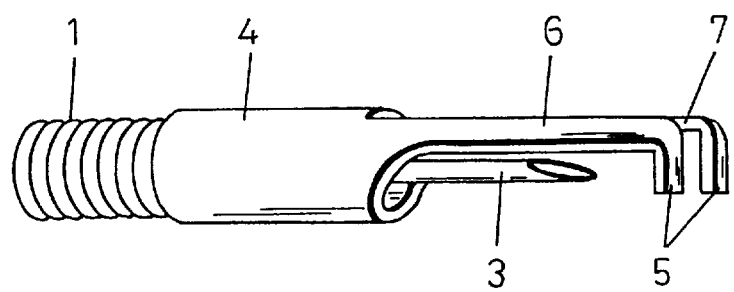
FIG. 3 is a perspective view of the distal end portion of the syringe according to the embodiment of the present invention, showing a state where the needle projects from the distal end of the sheath.

As shown in FIG. 3, the connecting member 6 and the mucous membrane holding member 5 are each split into two parallel arm-like portions by a splitting groove 7 extending parallel to the direction of the axis (i.e. the extension direction of the axis of the distal end portion of the sheath 1).

Referring to FIG. 2, the tubular member 4 is provided with an abutment wall 8 that is adapted to abut on the distal end surface of the sheath 1. The central portion of the abutment wall 8 is provided with a needle-passing hole having a diameter that allows the needle 3 to be loosely fitted therein and to pass therethrough.

The needle 3 has a stopper tube 9 secured to the outer peripheral surface thereof. The stopper tube 9 is made of a metal pipe and positioned such that it is located at the distal end of the sheath 1 when the distal end of the needle 3 projects as far as an intermediate portion of the connecting member 6.

The stopper tube 9 is formed with such an outer diameter that it cannot pass through the needle-passing hole provided in the abutment wall 8. Accordingly, when the stopper tube 9 abuts on the abutment wall 8, as shown in FIG. 2, the needle 3 cannot further project forward from the sheath 1.

Referring to FIG. 1, an operating part 10 is connected to the proximal end of the sheath 1. A sheath connecting tube 12 connected to the sheath 1 is screwed onto the distal end portion of the body 11 of the operating part 10.

An intermediate portion of the body 11 is provided with a slit 14 extending longitudinally. A slider 15 is secured to the proximal end portion of the fluid transfer tube 2. The slider 15 is slidably fitted in the slit 14.

The slider 15 has a pair of finger engagement portions 16 and 17 projecting outward from two opposite openings of the slit 14. The finger engagement portions 16 and 17 may be integral with the slider 15. Alternatively, the finger engagement portions 16 and 17 may be formed as separate members and connected to the slider 15. A thumb engagement portion 18 is provided on the rear end of the body 11.

Consequently, as the slider 15 is moved in the slit 14, as shown by the arrow B, with the operator's fingers engaged in the finger engagement portions 16, 17 and 18, the needle 3 moves axially, as shown by the arrow A, through the fluid transfer tube 2.

Figure 4:
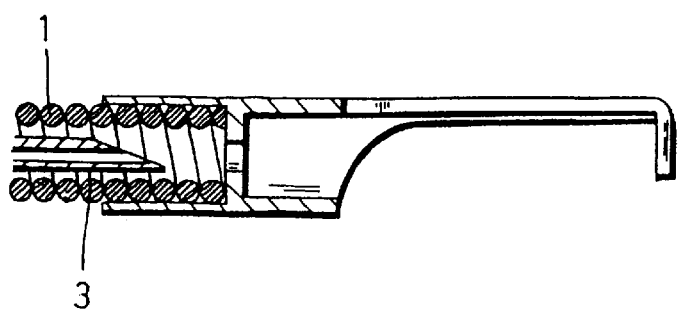
FIG. 4 is a sectional side view of the distal end portion of the syringe according to the embodiment of the present invention, showing a state where the needle is withdrawn from the distal end of the sheath.

Accordingly, actuating the slider 15 at the operating part 10 makes it possible to choose between a state where, as shown in FIG. 2, the needle 3 projects from the distal end of the sheath 1 and a state where, as shown in FIG. 4, the needle 3 is withdrawn into the distal end of the sheath 1.

As shown in FIG. 1, the proximal end of the fluid transfer tube 2 is communicated with a syringe tube-receiving socket 20 attached to the slider 15. Accordingly, if a liquid medicine, for example, is injected through a syringe tube (not shown) connected to the syringe tube-receiving socket 20, the liquid medicine passes through the fluid transfer tube 2 and flows out from the distal end of the needle 3. The arrangement may be such that the proximal end of the fluid transfer tube 2 is extended toward the proximal end of the body 11 from the portion of the fluid transfer tube 2 that is secured to the slider 15, and the syringe tube-receiving socket 20 is attached to the end of the extended fluid transfer tube 2.

Figure 5:
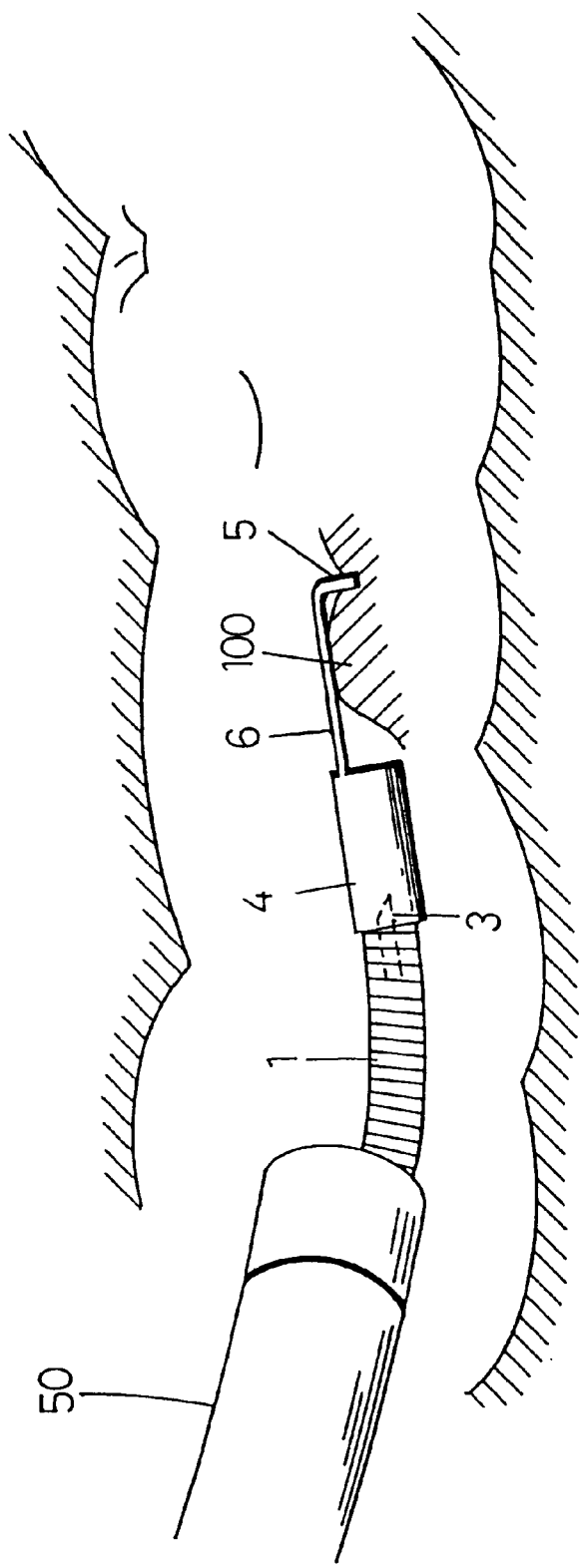
FIG. 5 is a schematic view showing the way in which the syringe according to the embodiment of the present invention is actually used.

In actual use of the syringe for an endoscope arranged as described above, as shown in FIG. 5, the distal end portion of the sheath 1 is projected from the distal end of the instrument-inserting channel of an endoscope 50, with the needle 3 withdrawn into the sheath 1. An affected part 100 that is to be stuck with the needle 3 is positioned in front of the distal end of the sheath 1. Then, the surface of the mucous membrane is held down with the mucous membrane holding member 5.

Figure 6:
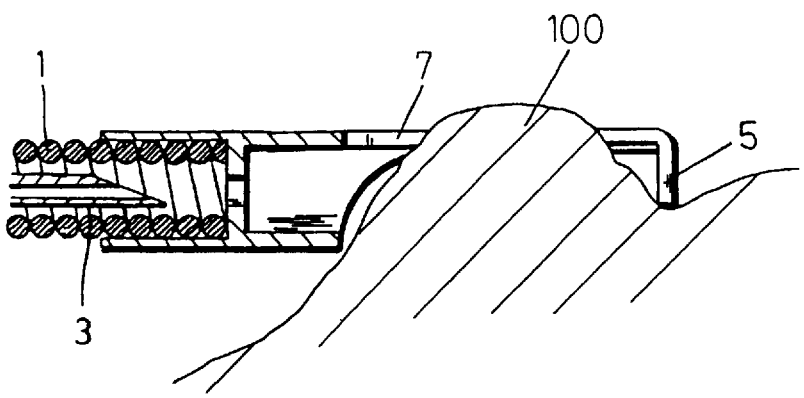
FIG. 6 is a sectional side view showing the distal end portion of the syringe according to the embodiment of the present invention under conditions of actual use.

Consequently, the positional relationship between the affected part 100 to be stuck with the needle 3 and the distal end of the sheath 1 is fixed. It should be noted that when the mucous membrane of the affected part 100 is soft, as shown in FIG. 6, the protuberant portion of the mucous membrane sticks out from the clearance defined by the splitting groove 7.

Figure 7:
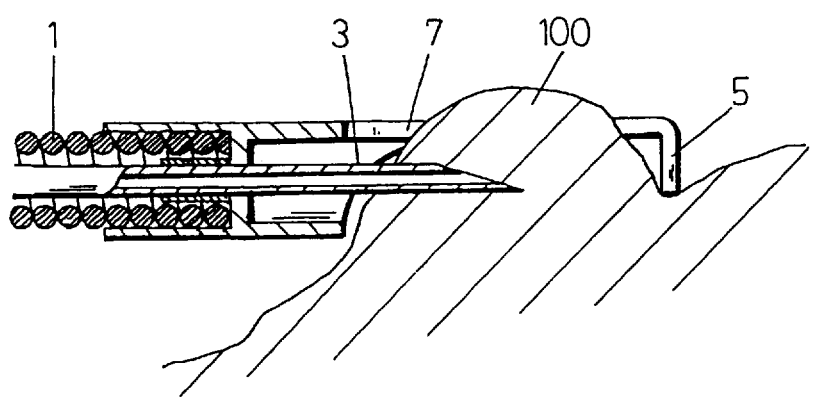
FIG. 7 is a sectional side view showing the distal end portion of the syringe according to the embodiment of the present invention under conditions of actual use.

When the distal end portion of the sheath 1 has been fixed with respect to the affected part 100, as shown in FIG. 7, the needle 3 is projected from the distal end of the sheath 1. Thus, the needle 3 can be accurately stuck into the affected part 100 to inject it with a liquid medicine or the like.

Figure 8:
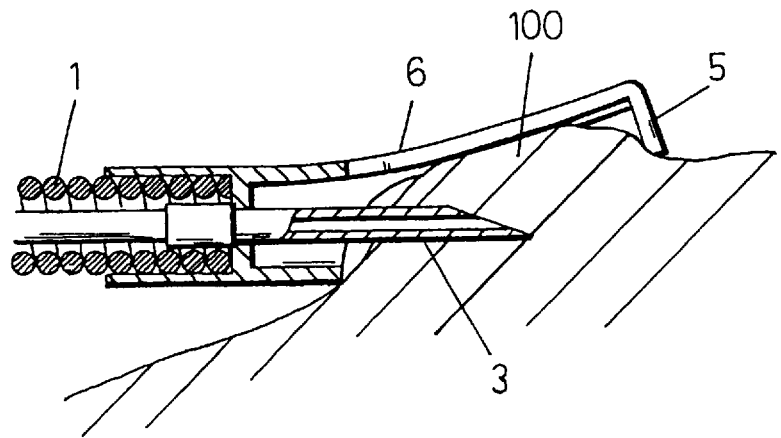
FIG. 8 is a sectional side view showing the distal end portion of the syringe according to the embodiment of the present invention under different conditions of use.

FIG. 8 shows the way in which the needle 3 is stuck into an affected part 100 that is not soft and is present on a slant surface of the mucous membrane. In this case, when the mucous membrane holding member 5 is pressed against the surface of the mucous membrane, the connecting member 6 is slightly warped by elastic deformation, and in this state, the sheath 1 is fixed with respect to the affected part 100. Under these conditions, the needle 3 can be accurately stuck into the desired position. After use, the connecting member 6 returns to the original straight shape.

According to the present invention, a mucous membrane holding member is provided at the distal end of the sheath through a connecting member in such a manner as to face the distal end of the sheath across a predetermined space. Consequently, the position of the distal end of the sheath can be fixed with respect the affected part by pressing the mucous membrane holding member against the mucous membrane even in a part of the body where the mucous membrane surface moves vigorously. Thus, the needle can be safely stuck into the correct position.

While the invention has been described by reference to a specific embodiment chosen for purposes of illustration, it should be apparent that numerous modifications could be made thereto by those skilled in the art without departing from the basic concept and scope of the invention.

What is claimed is:

1. A syringe for an endoscope comprising:
    a flexible sheath having an operating part connected to a proximal end portion thereof,
    a flexible fluid transfer tube axially movably inserted in said sheath;
    a hollow needle provided at a distal end of said fluid transfer tube in communication therewith, said needle being projected from and withdrawn into a distal end of said sheath by axially moving said fluid transfer tube with said operating part; and
    a connecting member having a proximal end and a distal end, said proximal end fixedly connected to the distal end of said sheath, and said distal end having a mucous membrane holding member adapted to be pressed against a mucous membrane surface, said mucous membrane holding member fixedly and substantially perpendicularly depending from said distal end of said connecting member, said mucous membrane holding member being positioned a fixed and predetermined distance from said distal end of said sheath and defining a space between said distal end of said sheath and said mucous membrane holding member, said mucous membrane holding member and said connecting member each split into two parallel arm-like portions having an axial groove extending between said arm-like portions, said groove defining a fixed distance between said arm-like portions.

2. A syringe according to claim 1 wherein said connecting member is adapted to warp by elastic deformation.

3. A syringe according to claim 1, further comprising:
    a stopper for limiting a maximum extent to which said needle projects from the distal end of said sheath.

4. A syringe according to claim 3, wherein when said needle projects from the distal end of said sheath to the maximum extent, a distal end of said needle lies between the distal end of said sheath and said mucous membrane holding member.

5. A syringe according to claim 1, further comprising:
a tubular member fitted and secured to the distal end of said sheath, wherein said tubular member, said mucous membrane holding member and said connecting member are integral with each other.

6. A syringe according to claim 1, wherein said sheath is formed from a close-wound coil pipe.

* * * * *